(12) United States Patent
Bokeriya et al.

(10) Patent No.: US 8,123,670 B2
(45) Date of Patent: Feb. 28, 2012

(54) METHOD FOR FORMING A BLOOD FLOW IN SURGICALLY RECONSTITUTED SEGMENTS OF THE BLOOD CIRCULATORY SYSTEM AND DEVICES FOR CARRYING OUT SAID METHOD

(76) Inventors: Leo Antonovich Bokeriya, Moscow (RU); Alexandr Yurievich Gorodkov, Moscow (RU); Gennady Iraklievich Kiknadze, Moscow (RU)

( * ) Notice: Subject to any disclaimer, the term of this patent is extended or adjusted under 35 U.S.C. 154(b) by 29 days.

(21) Appl. No.: 12/672,657

(22) PCT Filed: Aug. 9, 2007

(86) PCT No.: PCT/RU2007/000440
§ 371 (c)(1),
(2), (4) Date: Feb. 8, 2010

(87) PCT Pub. No.: WO2009/022940
PCT Pub. Date: Feb. 19, 2009

(65) Prior Publication Data
US 2011/0152599 A1  Jun. 23, 2011

(51) Int. Cl.
*A61M 1/10* (2006.01)
*A61F 2/82* (2006.01)
*A61F 2/24* (2006.01)
(52) U.S. Cl. ............ 600/16; 623/1.15; 623/2.1
(58) Field of Classification Search ............ 600/16; 623/1.15, 2.1
See application file for complete search history.

(56) References Cited

U.S. PATENT DOCUMENTS 4,857,046 A 8/1989 Stevens et al.
6,162,017 A 12/2000 Raible

FOREIGN PATENT DOCUMENTS

| RU | 2233632 C1 | 8/2004 |
|---|---|---|
| SU | 1362467 A1 | 2/1990 |
| SU | 1544418 A1 | 2/1990 |

*Primary Examiner* — Carl H. Layno
*Assistant Examiner* — Jon-Eric C. Morales
(74) *Attorney, Agent, or Firm* — Paul & Paul (57) ABSTRACT

The device relates to clinical cardiology and cardiovascular surgery. The method for forming a blood flow in research stands and in surgically reconstructed segments of the blood circulation system comprises diagnosing the individual condition of a patient's blood circulation system; measuring the blood flow velocity field in the heart chambers and great vessels; comparing the parameters measured against the physiological norm; determining parameters forming a swirled blood flow; and modeling an individual swirled blood current in the blood circulation system being diagnosed, the streamlined surfaces and guide elements of flow channels of the blood circulation system reconstructed being given shapes conforming to the flow lines of the restored normally swirled blood flow in accordance with formulas:

$$Q(t) = |z + Z_0(t)|r^2$$
$$\varphi = \varphi_0 + k(t)z$$
$$k(t) = \frac{\Gamma_0(t)}{4\pi Q(t)C_0(t)}$$
$$V_z = 2C_0(t)z$$
$$V_r = -C_0(t)r$$
$$V_\varphi = \frac{\Gamma_0(t)}{2\pi r}\left\{1 - \exp\left[\frac{-C_0(t)r^2}{2\nu}\right]\right\}.$$

15 Claims, 5 Drawing Sheets

METHOD FOR FORMING A BLOOD FLOW IN SURGICALLY RECONSTITUTED SEGMENTS OF THE BLOOD CIRCULATORY SYSTEM AND DEVICES FOR CARRYING OUT SAID METHOD

CROSS-REFERENCE TO RELATED APPLICATION

This is a national stage 371 application of International Application No. PCT/RU07/000,440, filed Aug. 9, 2007.

FIELD OF THE INVENTION

The invention relates to anatomy, physiology, and pathophysiology of blood circulation, clinical cardiology, and cardiovascular surgery.

The invention can be used for:

diagnosing blood circulation conditions and planning the tactics and scale of surgery in operations on the heart and vessels according to the criterion of restoration and maintenance of a physiological swirling structure of the blood flow;

designing organ-substituting implants used in cardiovascular surgery, including cardiac valve prostheses, blood vessel prostheses, a fully implanted artificial heart, and so on, which form and maintain a blood flow of a physiological swirling structure;

designing pumps, arteries, and cannulas used in assist and artificial blood circulation systems that form and maintain a required swirling blood flow structure; and modeling blood circulation physically for research and testing purposes allowing a flow of a model fluid or blood of desired swirling structure to be formed.

BACKGROUND OF THE INVENTION

Describing the blood flow structure and identifying the boundaries of physiological blood circulation norm is among the central problems of physiology, clinical pathophysiology, cardiology, and heart surgery.

The early results of studies of the structural blood flow organization were produced by high-speed filming of blood movement that visualized transport of radio-opaque compositions added to the blood stream. It was found that the blood flow had current lines corresponding frequently to a spiral and that the blood streams did not practically intermix in the central parts of the cardiovascular system, namely, the heart and great vessels. It was shown then that a normal blood flow was not turbulent, that it had a thin boundary layer on the walls of the flow channel, and that it was characterized by insignificant energy dissipation downstream.

As direct methods to measure blood velocity in the flow (electromagnetic flow meters, film thermo-anemometers, and Doppler ultrasonic pulse velosymmetry) came into use, it was established that both the insignificant thickness of the boundary layer and the complex profile of longitudinal velocities in the heart and aorta do not unambiguously confirm that the flow is either laminar or turbulent.

In the latter half of the 1970s, morphological studies and physical modeling, along with cine-angiography and ventriculography helped to discover:

asymmetric conjugation of the principal cavities in the main part of the cardiovascular system that helps swirl the stream;

spiral orientation of some of the intracardiac trabeculas;

fragmentary visualization of blood flow swirling in the central circulation parts; and spiral orientation of the nuclei of endothelial cells in the aorta corresponding to the direction in which shear stresses are applied.

These findings led to an assumption that the blood in the central parts of the circulation system flows in the form of a swirled stream, and yet direct visualization and determination of the structure of a real or modeled flow were unsuccessful.

Development of new methods to study fluid flows (MP-tomography and MP-velosymmetry, color Doppler-echocardiography, and laser anemometry) offered opportunities for three-dimensional measurement of the velocities in the blood flow. For example, color Doppler-echocardiography showed swirling in the blood flow in the aorta, and MP-velosymmetry registered episodes of an axisymmetric swirled blood flow in the heart and several major arteries. These studies, too, failed to provide a quantified description of the blood flow because of the absence of analytical or numerical methods for modeling current in a channel of complex geometric configuration such as a blood stream.

Still, a number of products were offered for heart surgery on the basis of empirical observations suggesting flow swirling to improve their functional characteristics.

In the absence of an adequate hydrodynamic model of swirled flow, designers of these products could not use quantified ratios associating blood flow characteristics with the geometry of the flow channel of the streams formed. Besides, these assumptions disregarded the structural specifics and the non-stationary nature of the swirled blood flow.

As a result, the flow modeled on the basis of these assumptions could not restore the normal hydrodynamic characteristics of the blood circulation system without producing stagnation zones and flow separation zones that are factors provoking thrombosis, blood injury, and hyperplasia in the blood stream.

The proposals described below as prior art could not, therefore, be used as functionally complete organ-substituting devices for the cardiovascular system.

In particular, a method currently known to be used to form a blood flow at the cannula outlet was chosen as immediate prior art (Patent RU 2233632 C1, Aug. 10, 2004). The desired effect is achieved, in the view of the inventors of the prior art device, by forming a rotationally translational blood flow in a curved serpentine channel so that the flow actively interacts with the curved walls of the channel and receives a swirl. According to the inventors, blood flow swirling by their method is maintained over a length of the downstream rectilinear portion.

The prior art method, however, does not create conditions in which a flow swirled around the axis of a curved channel develops and maintains rotation around its own axis of symmetry. The method disregards the considerable losses of flow energy as the flow interacts with the wall, nor does it have the conditions to prevent formation of stagnation zones. All parameters of flow swirling are of a speculative, qualitative nature, and are not supported experimentally.

Apart from the above, the prior art method has the following drawbacks:

absence of conditions for the parameters of the swirled blood flow and cannula design (radius, curvature and pitch of flow swirling, and so on) to conform to the patient's individual blood circulation norms;

absence of desired boundary conditions of the swirled flow in the cannula to define conditions for interaction between the blood flow and the walls of the flow channel;

absence of desired initial conditions needed to form a swirled flow in the coil, which conditions determine the velocity field in the flow, its space and time characteristics, the shape of the flow channel, and direction of flow;

disregard for the non-stationary nature of the flow such as changes in the flow velocity components over the cardiac cycle; and restriction of the possible types of cannulas to a single design of the prior art invention.

The cannula of the immediate prior art invention allows, in the inventors' view, a right- or left-hand swirl to be given to blood flowing through a spiral-shaped coil. This invention cannot be exercised because the flow takes a direction corresponding to the spatial orientation of the coil walls and cannot be swirled around its own axis, for which reason it is not a swirled flow.

A prior art vessel prosthesis comprises a tube provided on the inside surface with a relief to swirl the blood flow (Patent RU 2153360 C2, Feb. 27, 1995). This prior art prosthesis is disadvantageous because it cannot produce a blood flow having desired characteristics corresponding to the patient's individual norms.

A prior art heart valve prosthesis comprises elements to direct the blood flow, said elements possibly having an axial symmetry and curved cusps and/or body so that a swirled flow is formed as blood flows around them (WO 02/062271).

The prior art device is disadvantageous because it does not provide conditions for joining the flow upstream of the valve, at the valve, and downstream of the valve. This inconsistency leads to further energy losses and flow disturbance at the valve, increasing the risk of thrombosis and blood injury and lowering the functional characteristics of the device.

A prior art pump for an assist blood circulation system that forms a swirled blood flow comprises a chamber having valves arranged opposite one another and a guide in the form of an Archimedean spiral (GB 2,371,230, Jul. 24, 2002).

This device is disadvantageous because it lacks conditions for joining currents upstream and downstream of the pump, for which reason it cannot prevent formation of stagnation zones and flow separation zones and, therefore, it increases the risk of thrombosis and blood injury in the through-flow chamber of the pump.

A prior art swirling device in the form of a nozzle has guide elements on the inside surface thereof (Patent SU 699125 A, Nov. 30, 1979). This device is disadvantageous because it cannot be used to form a flow of blood or model fluid having desired swirling characteristics.

SUMMARY OF THE INVENTION

A quantitative analysis of blood circulation in general and the structure of blood flow in the human heart and great vessels, and also this invention became possible after precise solutions had been found for basic non-stationary equations in viscous fluid hydrodynamics (Kiknadze G. I., Krasnov Yu. K., Evolution of a Spout-Like Flow of a Viscous Fluid, Sov. Phys. Dokl., 1986; 31(10): 799-801). The solutions led to the description of blood flow formation and evolution in the human heart and great vessels in sufficient detail. The present invention is based on this description.

The technical result of the claimed method consists in:

developing software tools and mathematical support for measuring the quantified characteristics of a swirled blood flow on the basis of exact solutions of non-stationary hydrodynamic equations for swirled flows of viscous fluid to diagnose blood circulation conditions, treat diseases of the cardiovascular system, design implantable and para-corporeal organ-substituting devices for use in heart surgery, and set up research and testing stands to simulate various blood circulation conditions;

developing methods for analyzing blood circulation conditions by exact solutions of non-stationary hydrodynamic solutions for swirled flows and building a database of individual blood circulation norms based on the conception of a swirled blood flow structure;

developing principles for planning and developing tactics for surgical treatment of patients with cardiac and vascular pathologies in order to restore their blood circulation conditions to their individual norms by repairing and maintaining a swirled blood flow structure;

developing a method for forming a blood flow of a desired structure corresponding to the exact solutions of non-stationary hydrodynamic equations for swirled flows of viscous fluid as they flow around the devices implanted in the blood stream and when blood circulation is modeled in experimental stands;

designing implantable and para-corporeal devices for cardiovascular surgery allowing individual blood circulation norms to be restored partially or fully by forming a physiological swirled blood flow structure; and designing research and testing stands simulating a wide range of blood circulation conditions, including a swirled flow of blood or model fluid.

The technical result achieved by using the claimed method is based on the established fact that the blood flow in the circulation system of humans and animals is a swirled stream. The velocity field and pressure field in this stream have been determined by exact solution of non-stationary equations of viscous fluid hydrodynamics (see: the article by Kiknadze G. I., Krasnov Yu. K., Evolution of a Spout-Like Flow of a Viscous Fluid, Sov. Phys. Dokl., 1986; 31(10) already cited above). The researchers discovered mechanisms that help form and regulate a swirled stream in the heart and great vessels (Kiknadze G. I., Oleinikov V. G., Gachechiladze I. A., Gorodkov A. Yu., Dobrova N. B., Bakei Sh., Bara Zh.-L., "The Structure of the Flow in the Left Ventricle and Aorta on the Basis of Exact Solutions of Non-Stationary Hydrodynamic Equations and Morphometric Studies," Reports of the Academy of Sciences (Far Eastern Branch), 1996, Vol. 351, pp. 119-122); calculated the quantified values of the basic parameters of the normal swirled blood stream in the aorta of healthy volunteers (Gorodkov A. Yu., Nikolayev D. A., "An Analysis of the Dynamic Characteristics of a Swirled Blood Flow on the Basis of Measurement of the Geometric Parameters of a Flow Channel by MP Tomography," Bulletin of the Bakulev Science Center, Russian Academy of Medical Sciences, No. 9, 2003, pp. 67-69; Bokeria L. A., Gorodkov A. Yu., Kiknadze G. I., et al., "An Analysis of the Velocity Field of a Swirled Blood Flow in the Aorta on the Basis of Three-Dimensional Mapping by MP Velosymmetry," Bulletin of the Bakulev Science Center, Russian Academy of Medical Sciences (RAMS), No. 9, 2003, pp. 70-74). The findings of the latest studies have shown that exact solutions of non-stationary hydrodynamic equations reflect adequately the conditions of blood circulation in the normal and in pathology, in which case the principal compensatory factor characterizing the heart remodeling process is flow circulation that depends on the azimuthal velocity component. In particular, they show the possibility of mitral stenosis being compensated up to 90% or the mitral valve being regurgitated up to 85% by altering the azimuthal velocity component (Bokeria L. A., Gorodkov A. Yu., Kiknadze G. I, Nikolayev D. A. Klyuchnikov I. V., Alshibaya M. D., "An Analysis of Mechanisms for Compensating and Remodeling the Left Ventricle in Case of Pathological Change of the Cavity Geometry," 11th Scientific Session of the Bakulev Science Center, Russian Academy of Medical Sciences, Moscow, May 13-15, 2007, Bulletin of the Bakulev Science Center, RAMS, Vol. 8, No. 3, 2007: 200). Exact solutions, therefore, help carry out an analysis of blood circulation in different conditions of the cardiovascular system.

The pattern of blood flow swirling and mechanisms to form the blood flow discovered were studied experimentally and theoretically and identified for a physiologically normal condition of the organism. Moreover, use was made of posthumous morphological measurements of the heart and aorta, dynamic reconstruction of the aorta by MP tomography, measurements of the blood flow velocity field in the aorta of healthy volunteers by MP velosymmetry, and quantified analysis of a swirled blood flow using exact Kiknadze-Krasnov solutions describing such flows.

The above technical result is achieved by using the method of this invention for forming a blood flow in surgically reconstructed segments of the blood circulation system, which method consists in diagnosing the individual condition of a patient's blood circulation system; measuring the velocity field of the blood flow in the heart chambers and great vessels; comparing the parameters measured against the physiological norm; determining parameters that form a swirled blood flow; and modeling the individual swirled blood flow in the blood circulation system diagnosed and in testing stands, the streamlined surfaces and the guide elements of the flow channels of the blood circulation system to be reconstructed being given shapes corresponding to the lines of flow of the restored normally swirled blood flow in accordance with the following equations:

$$Q(t) = [z + Z_0(t)]^2 \quad (1.1)$$

$$\varphi = \varphi_0 + k(t)z \quad (1.2)$$

$$k(t) = \frac{\Gamma_0(t)}{4\pi Q(t)C_0(t)} \quad (1.3)$$

$$V_z = 2C_0(t)z(t) + C_1(t) \quad (2.1)$$

$$V_r = -C_0(t)r(t) \quad (2.2)$$

$$V_\varphi = \frac{\Gamma_0(t)}{2\pi r(t)} + \sum_i \left[\frac{\Gamma_i(t)}{2\pi r(t)}\right] \cdot [\Psi[(C_1(t)+1), \beta_i(t)r^2]] \quad (2.3)$$

wherein: $V_r$, $V_z$, and $V_\varphi$ are the radial, longitudinal, and tangential components of the swirled flow velocity; v is the kinematic viscosity of the medium; $\varphi_0$ is the initial swirling angle relative to the flow radius; $\varphi$, z and r current values of the angular, longitudinal, and radial coordinates along the flow line; and Q(t), $Z_0(t)$, k(t), $T_0(t)$ and $C_0(t)$ are parameters of the swirled blood flow depending on time by virtue of the non-stationary flow pattern and corresponding to individual norms for a physiological swirled blood flow.

The blood flow is diagnosed by any, including ultrasonic and magnetic resonance, methods for measuring changes in velocity, the software for performing a selected blood flow measurement method being based on the use of exact solutions of non-stationary hydrodynamic equations for swirled flows of viscous fluid and helping build a database of normal indicators; determine the limits of the compensatory reserve of the patient's blood circulation system; justify decompensation criteria according to the parameters Q(t), $Z_0(t)$, k(t), $\Gamma_0(t)$ and $C_0(t)$ of a swirled blood flow; characterization of the patient's blood circulation condition at the stages of treatment planning and result evaluation; and development of design documents for making any devices related to the swirled structure of the blood flow.

The streamlined surfaces and guides in the flow channels of the devices are provided with a relief consisting of areas of originally smooth surface alternating with curved areas in the form of depressions, each formed by quadric convex and concave surfaces joined along their common tangents. Moreover, a depression is joined to the originally smooth surface by convex surfaces forming slopes for which the originally smooth surface in the joint areas is a tangent.

The streamlined surfaces and guide elements of the system to be reconstructed are movable and/or elastic.

The technical effect achieved by using the vessel prosthesis of this invention is causing blood to flow inside the prosthesis in a stream identical in structure to a physiological swirled flow that is free from stagnation and separation zones and reducing the risk of thrombosis, blood injury, and hyperplasia in the prosthesis implantation area.

The vessel prosthesis comprises a tube having an internal surface provided with a relief to swirl the blood flow in accordance with formulas (1.1 to 1.3) and localization of the segment to be reconstructed.

The internal surface of the prosthesis is provided with a relief consisting of areas of originally smooth surface alternating with curved areas in the form of depressions, each formed by quadric convex and concave surfaces joined along their common tangents. Moreover, a depression is joined to the originally smooth surface by convex surfaces forming slopes for which the originally smooth surface in the joint areas is a tangent.

The tube may be made of an elastic bio- and hemo-compatible material, for example, woven synthetic fabric, that maintains conformity of the shape of flow section area to the time-dependent blood flow norms Q(t) and $Z_0(t)$ along the vessel channel during the entire cardiac cycle.

The technical effect produced by using the cannula of this invention is maintaining a blood flow inside the cannula that is identical in structure to the physiological swirled flow that is free from stagnation and separation zones and reduces the risk of thrombosis, blood injury, and channel hyperplasia in the prosthesis implantation area. Moreover, the blood flow at the inlet and outlet of the cannula is combined (joined) in terms of velocity and pressure values with the blood flow entering the cannula and the blood flow in the vessel downstream of the cannula.

A cannula for para-corporeal perfusion devices comprises a flow channel having an internal surface provided with a longitudinal blood-swirling relief of a shape described by formulas (1.1 to 1.3) that depend on the specific localization of the point where the cannula is inserted into the vessel channel.

The internal surface of the cannula may be provided with a relief consisting of areas of originally smooth surface alternating with curved areas in the form of depressions, each produced by quadric convex and concave surfaces joined along their common tangents. Moreover, a depression is joined to the originally smooth surface by convex surfaces having slopes for which the originally smooth surface in joint areas is a tangent.

A length of the channel may have guides in the form of ribs, grooves or blades of a shape determined by formulas (1.1 to 1.3) in accordance with the specific localization of the point where the cannula is inserted into the vessel channel.

The cannula may be made of an elastic material of flexibility that helps maintain conformity of the parameters Q(t) and $Z_0(t)$ to individual blood circulation norms along the flow channel of the cannula at every moment of the cardiac cycle.

The technical effect produced by using the heart valve prosthesis of this invention is blood flow through the prosthesis that is identical in structure to the physiological swirled blood flow free from stagnation and separation zones and reducing the risk of thrombosis and blood injury.

The heart valve prosthesis comprises one or more shutoff elements located in a symmetric central position in a body of round and/or oval cross-section, the streamlined surfaces of the valve being provided with a pattern of formulas (1.1 to 1.3).

The streamlined surfaces of the shutoff elements and body of the valve are provided with a relief consisting of areas of originally smooth surface alternating with curved areas in the form of depressions, each formed by quadric convex and concave surfaces joined along their common tangents. Moreover, a depression is joined to the originally smooth surface by convex surfaces producing slopes for which the originally smooth surface in the joint areas is a tangent.

The technical effect produced by the blood pump of this invention is maintaining a swirled flow free from stagnation and separation zones in the pump working chamber and at the outlet thereof so that the risk of thrombosis and blood injury is reduced. The flow formed in the pump is combined (joined) at the pump inlet and outlet, in terms of velocity field and pressure, with the blood flows at the connection points thereof.

The blood pump comprises a flow swirling unit, a flow channel, and valves at the channel inlet and outlet, the surface washed over by blood being provided with a relief that varies over time according to formulas (1.1 to 1.3).

The pump surfaces washed over by blood are provided with a relief consisting of areas of originally smooth surface alternating with curved areas in the form of depressions, each formed by quadric convex and concave surface joined along their common tangents. Moreover, a depression is joined to the originally smooth surface by convex surfaces producing slopes for which the originally smooth surface in the joint areas is a tangent.

The blood pump is provided in the inlet part of the flow channel thereof with guides in the form of ribs, grooves or blades of a geometric shape that is determined by formulas (1.1 to 1.3) and is identical to the parameters of the diastolic flow.

The blood pump is provided in the outlet part of the flow channel thereof with guides in the form of ribs, grooves or blades of a geometric shape that is determined by formulas (1.1 to 1.3) and is identical to the parameters of the systolic flow. Moreover, the relief corresponding to the systolic expulsion from, and the relief corresponding to the diastolic filling of, the pump working chamber have a gradual transition from one to the other.

The pump valves may be patterned on the design of the heart valve prostheses described above.

The pump channel may be patterned on the design of the cannula described above.

The technical effect produced by the use of the swirling device of this invention is forming a swirled flow of blood or model fluid having a desire velocity and pressure field corresponding to the different blood circulation conditions being modeled.

The swirling device comprises an end piece having a streamlined surface that is provided with guides in the form of ribs, grooves or blades of a shape determined by formulas (1.1 to 1.3), the swirling angle of the guides relative to the flow axis being optionally varied by the operator or a device adapted to model different flow conditions.

The device surfaces washed over by blood may be provided with a relief consisting of areas of originally smooth surface alternating with curved areas, each formed by quadric convex and concave surfaces joined along common tangents, the depressions being joined to the originally smooth surface by convex surfaces producing slopes for which the originally smooth surface in joint areas is a tangent.

DESCRIPTION OF EMBODIMENTS OF THE INVENTION

It has been demonstrated by morphological, functional, and experimental methods that the pulsating blood flow in the heart and great vessels has a swirled structure that allows blood to be transported without energy losses and formation of flow separation and stagnation zones.

A quantitative analysis of the structure of a blood flow being formed, and the mechanisms for generating it and its evolution in the heart and great vessels undertaken by exact solutions of non-stationary hydrodynamic flows of a viscous fluid (Kiknadze G. I., Krasnov Yu. K., Evolution of a Spout-Like Flow of a Viscous Fluid, Sov. Phys. Dokl. 1986; 31(10): 799-801), helped, on the basis of experimental and clinical studies, to prove consistency of the resultant exact solutions with the well-known patterns of blood circulation physiology. As a result, a conception was formulated to match the specificities of swirled blood flow and blood circulation function (Kiknadze G. I., Oleinikov V. G., Gachechiladze I. A., Gorodkov A. Yu., Dobrova N. B., Bakei Sh., Bara Zh.-L., "The Structure of the Flow in the Left Ventricle and Aorta on the Basis of Exact Solutions of Non-Stationary Hydrodynamic Equations and Morphometric Studies," Reports of the Academy of Sciences (Far Eastern Branch), 1996, Vol. 351, pp. 119-122; and Gorodkov A. Yu., "An Analysis of the Structure of the Intracardiac Swirled Blood Flow on the Basis of Morphometry of the Trabecular Relief of the Left Heart Ventricle," Bulletin of the Bakulev Science Center, RAMS, No. 9, 2003, pp. 63-66).

The modern concept of the nature of swirled blood flow in the heart, aorta, and great arteries is that, as is argued above, a swirled stream formed at the heart outlet and evolving during cardiac contraction under the effect of the intracardiac trabecular relief, is the principal component of blood flow in physiological normal conditions. Passage of the swirled stream in the blood channel results in the formation of stable localized back and secondary currents, and still the resultant flow moves in the aorta without producing separation and stagnation zones and causes a physiologically normal distribution of blood to regional pools. Moreover, the resultant flow contains a totality of all swirled currents described by formulas (2.1 to 2.3) in the same manner as the dominant swirled stream expelled from the heart as a result of cardiac contraction.

Depending on the form and spatial orientation of the trabeculas and papillary muscles, a swirled blood flow is formed in the heart chambers in the shape of a spout-like stream characterized by a radial velocity gradient $C_0(t)$, blood circulation in the vortex $\Gamma_0(t)$, and initial coordinate $Z_0(t)$ in accordance with the exact Kiknadze-Krasnov solutions of non-stationary hydrodynamic equations for the class of swirled flows:

$$V_z = 2C_0(t)z(t) + C_1(t) \tag{2.1}$$

$$V_r = -C_0(t)r(t) \tag{2.2}$$

$$V_\varphi = \frac{\Gamma_0(t)}{2\pi r(t)} + \sum_i \left[\frac{\Gamma_i(t)}{2\pi r(t)}\right] \cdot [\Psi[(C_1(t)+1), \beta_i(t)r^2]] \tag{2.3}$$

wherein: $V_r$, $V_z$, and $V_\varphi$ are the radial, longitudinal, and tangential components of the swirled flow velocity; $r(t)$, $z(t)$ and $\varphi(t)$ are cylindrical coordinates having their origin combined with the single point $Z_0(t)$ within the flow channel, at which $V_r=V_z=V_\varphi=0$, the position of said point changing in time and moving along the flow;
$C_0(t)$, $\Gamma_0(t)$ and $\Gamma_i(t)$ are individual characteristics of the swirled flow, that is, respectively, the radial velocity gradient, major circulation, and multiple i-th circulations of the medium in the swirled flow originating in the composition of vortexes combined by a single dominant circulation;
$\psi[(C_1+1), \beta_i(t)r^2]$ is Euler's incomplete gamma function responsible for energy dissipation in the swirled flow of a viscous fluid that governs this process through an individual factor for each flow:

$$\beta_i(t) = \beta_i(0)\exp\left\{-\frac{2\int_\tau C_0(\tau)d(\tau)}{1-4\nu\beta_i(0)\int_\tau d\tau \cdot \exp[-2\int_{\tau'}C_0(\tau')d\tau']}\right\},$$

wherein: $\nu$ is the kinematic viscosity of the medium involved in the swirled current.

The Cauchy-Euler integral, which represents a change in pressure for such currents in the cardiac cycle, in particular, when $C_1(t)=0$, $\Gamma_0(t)=\Gamma_1(t)$ is the dominant circulation and all remaining circulations beginning with $\Gamma_2(t)=0$. In other words, the Cauchy-Euler integral defining a change in pressure in the dominant swirled stream has the form:

$$P(t) = p_0 + \rho u + \frac{\rho C_0(t)(R^2 + 4z^2)}{2} +$$
$$\frac{\rho d C_0(t)}{dt}\left(\frac{R^2}{2} + z^2\right) + \frac{\rho \Gamma_0^2}{8\pi^2 \nu} \cdot \left[E_1\left(\frac{C_0(t), R^2}{\nu}\right) - E_2\left(\frac{C_0(t), R^2}{2\nu}\right)\right]$$

wherein: $E_1$ and $E_2$ are known integral exponentials $$E_n(t) = \int_0^\infty t^{-n} e^{-xt} dt$$

of the n-th order.

The current (2.1 to 2.3) discovered carries potential in the longitudinal and radial direction and, for this reason, is accompanied by insignificant dissipation of flow energy occurring only in the narrow zone around the axis of the swirled stream, the cross-section (radius) of said zone being defined by the formula:

$$R_0 = \sqrt{\frac{2\nu k}{C_0}},$$

wherein: k is the dissipation coefficient. Viscosity and current velocity in the blood flow having characteristic values, the radius $R \approx 1.5$ to 2.0 mm When, therefore, a swirled blood stream has a radius of 10 to 25 mm, corresponding to the characteristic dimensions of the flow channel for the aorta and the left ventricle, energy dissipation is negligibly small, and the blood current is practically quasi-potential.

Observations of the swirled stream formed in the heart indicate that this stream has a single circulation and dominates inside the aorta for a considerable part of the cardiac cycle, surrounded by back swirled currents having residual circulations of the preceding cardiac cycle determined similarly by formulas (2.1 to 2.3). The dominant steam has a single circulation $\Gamma_0$ acquired owing to the spiral spatial orientation of the trabeculas and papillary muscles inside the left ventricle of the heart that form the swirled blood flow described by formulas (3.1 to 3.3) that is expelled.

$$V_z = 2C_0(t)z \tag{3.1}$$

$$V_r = -C_0(t)r \tag{3.2}$$

$$V_\varphi = \frac{\Gamma_0(t)}{2\pi r}\left\{1 - \exp\left[\frac{-C_0(t)r^2}{2\nu}\right]\right\} \tag{3.3}$$

wherein: Vr, Vz, V$\varphi$, r, z, $\varphi$, $C_0(t)$, $\Gamma_0(t)$ and $\nu$ are as defined above.

Conformity of the structure of the physiological swirled blood flow to the exact Kiknadze-Krasnov solutions has been demonstrated morphologically and by clinical functional studies. The right parts of the heart are governed by similar patterns.

Indeed, A. Yu. Gorodkov (Gorodkov A. Yu., "An Analysis of the Structure of the Intracardiac Swirled Blood Flow on the Basis of Morphometry of the Trabecular Relief of the Left Heart Ventricle," Bulletin of the Bakulev Science Center, RAMS, No. 9, 2003, pp. 63-66) performed an analysis of the spatial architectonics of the flow channel of the left cardiac ventricle. He found, from the combination of features characterizing different phases of the cardiac cycle, that the trabecular relief of the left ventricle shows two independent spirally organized systems of trabeculas: one shows up as the myocardium is tensioned in the systole, and the other is evident during diastolic relaxation of the myocardium. These two trabecular systems are oriented along the flow lines defined by formulas (3.1 to 3.3) and fulfill the role of guide blades that form a swirled blood stream during the cardiac cycle. As the left ventricle is filled, blood flows around the structural elements of the free wall made up of trabeculas forming the diastolic filling profile; and when the heart contracts, the tension of the papillary muscles and longitudinal trabeculas in the front wall of the left ventricle generates a flow and directs it to the alternative relief that produces a flow to be expelled into the aorta. The spatial organization of trabeculas corresponds, during ventricle filling and blood expulsion into the aorta, to the form of flow lines of the Kiknadze-Krasnov swirled current.

A. Yu. Gorodkov and D. A. Nikolayev (Gorodkov A. Yu., Nikolayev D. A., "An Analysis of the Dynamic Characteristics of a Swirled Blood Flow on the Basis of Measurement of the Geometric Parameters of a Flow Channel by MP Tomography," Bulletin of the Bakulev Science Center, RAMS, No. 9, 2003, pp. 67-69) provide intravital measurements of the geometry of the aorta flow channel by MP tomography. The contours of a series of channel sections were used to perform a dynamic three-dimensional reconstruction of the aorta. Adequacy of the reconstruction was verified by measuring the radius of the inlet area and the volume and length of the aorta segment reconstructed, The results show that variations in these values over a single cardiac cycle agreed with the logic of cardiac contraction and blood expulsion into the aorta.

In another study (Bokeria L. A., Gorodkov A. Yu., Kiknadze G. I., Nikolayev D. A., Gachechiladze I. A., "An Analysis of the Velocity Field of a Swirled Blood Flow in the Aorta on the Basis of Three-Dimensional Mapping by MP Velosymmetry," Bulletin of the Bakulev Science Center, RAMS, No. 9, 2003, pp. 70-74), an analysis of the velocity field in the aorta was performed on the basis of MP velosymmetry. The characteristics of the swirled blood flow calculated on the basis of experimental data have shown that the current lines in the aorta are an uninterrupted continuation of the systolic trabecular relief of the left ventricle. All these facts lead to the conclusion that the blood flow in the left ventricle and aorta corresponds in structure to the class of Kiknadze-Krasnov swirled currents.

The studies conducted give reasons to argue that the exact Kiknadze-Krasnov solutions used as the principal quantitative criterion is the only method for forming a physiological blood flow in both the blood channels and implants for cardiovascular surgery.

This method allows hydrodynamic compatibility with the physiological flow, prevents formation of stagnation and separation zones, reduces the risk of thrombosis and blood injury, and prevents plastic changes in the channel in case of inadequate distribution of shear stresses in the walls.

Accordingly, this invention relates to a method for diagnosing the blood circulation conditions and treatment of heart and vascular diseases by forming a swirled blood flow. This blood flow is to be formed in accordance with individual norms during reconstruction operations on the heart and vessels, and also in the designs of implants for the cardiovascular system, using the exact Kiknadze-Krasnov solutions of non-stationary hydrodynamic equations of the class of swirled currents as a quantitative criterion.

The method for forming a blood flow in surgically reconstructed segments of the blood circulation system consists in diagnosing the individual condition of a patient's blood circulation system; measuring the blood flow velocity field in the heart chambers and great vessels; measuring the parameters forming a swirled blood flow; and modeling an individual blood flow in the blood circulation system being diagnosed, the streamlined surfaces and guide elements of the flow channels of the blood circulation system reconstructed being given shapes corresponding to the flow lines of the reconstructed normally swirled blood current in accordance with formulas (1.1 to 1.3 an 3.1 to 3.3).

The blood flow is diagnosed by any methods, including ultrasonic and magnetic resonance techniques, for measuring velocity, the software tools of the selected blood flow measurement method being based on the use of exact solutions of non-stationary hydrodynamic equations for swirled flows of a viscous fluid and building a database of normal indicators, determining the limits of the compensatory reserve of the patient's blood circulation system, justifying decompensation criteria according to parameters $Q(t)$, $Z_0(t)$, $k(t)$, $\Gamma_0(t)$ and $C_0(t)$ of the swirled blood flow, the characteristic of the patient's blood circulation condition at the stages of planning, and assessing the result of, treatment, and also developing design documents for making any devices adapted for the swirled blood flow structure.

The streamlined surfaces and guides are provided with a relief consisting of areas of originally smooth surface alternating with curved areas in the form of depressions, each formed by quadric convex and concave surfaces joined along common tangents. Moreover, a depression is joined to the originally smooth surface by convex surfaces producing slopes for which the originally smooth surface in the joint areas is a tangent.

The streamlined surfaces and guide elements of the system being reconstructed are movable and/or elastic.

The vessel prosthesis comprises a tube having an internal surface that is provided with a pattern for swirling the blood flow in accordance with formula (1.1) for a specific localization of the segment to be replaced with a prosthesis.

The internal surface of the prosthesis is provided with a relief consisting of areas of originally smooth surface alternating with curved areas in the form of depressions, each produced by quadric convex and concave surfaces joined along common tangents. Moreover, a depression is joined to the originally smooth surface by convex surfaces producing slopes for which the originally smooth surface in the joint areas is a tangent.

The tube can be made of an elastic bio- and hemo-compatible material, for example, a woven synthetic fabric, that makes the shape of the flow section of the blood flow channel consistent with the normal current parameters $Q(t)$ and $Z_0(t)$ along the vessel channel over the entire cardiac cycle.

A cannula for para-corporeal perfusion devices comprises a flow channel having an internal surface provided with a longitudinal relief for swirling the blood flow in accordance with equations (1.1 to 1.3), depending on the specific localization of the point where the cannula is inserted into the vessel channel.

The internal surface of the cannula may be provided with a relief consisting of areas of originally smooth surface alternating with curved areas in the form of depressions, each formed by quadric convex and concave surfaces joined along common tangents. Moreover, a depression is joined to the originally smooth surface by convex surfaces producing slopes for which the originally smooth surface in the joint areas is a tangent.

A part of the channel may contain guides in the form of ribs, grooves or blades having a swirling angle described by equations (1.1 to 1.3), depending on the specific localization of the point where the cannula is inserted into the vessel channel.

The cannula may be made of an elastic material of flexibility that keeps the parameters Q(t) and $Z_0(t)$ consistent with individual norms along the length of the flow channel at every moment of the cardiac cycle.

A heart valve prosthesis comprises one or more shutoff elements arranged symmetrically in the center of a body of round and/or oval cross-section, the streamlined surfaces of the valve being provided with a pattern in accordance with equations (1.1 to 1.3).

The streamlined surfaces of the shutoff elements and body of the valve are provided with a relief consisting of areas of originally smooth surface alternating with curved areas in the form of depressions, each formed by quadric convex and concave surfaces joined along common tangents. Moreover, a depression is joined to the originally smooth surface by convex surfaces producing slopes for which the originally smooth surface in the joint areas is a tangent.

A blood pump comprises a flow channel and valves at the inlet and outlet of the channel, the surface washed over by blood being provided with a relief that changes downstream of the flow in accordance with equations (1.1 to 1.3).

The pump surfaces washed over by blood are provided with a relief consisting of areas of originally smooth surface alternating with curved areas in the form of depressions, each formed by quadric convex and concave surfaces joined along common tangents. Moreover, a depression is joined to the originally smooth surface by convex surfaces producing slopes for which the originally smooth surface in the joint areas is a tangent.

The pump further comprises in the outlet part of the streamlined surface of the flow channel guides in the form of ribs, grooves or blades having a swirling angle:

$$\phi = \phi_0 + k_s(t)z,$$

wherein: $k_s(t)$ is a time-dependent parameter of the swirled blood flow corresponding to the normal indicator for the systolic flow.

The inlet part of the streamlined pump surface is provided with guides in the form of ribs, grooves or blades having a swirling angle:

$$\phi = \phi_0 + k_d(t)z,$$

wherein: $k_d(t)$ is a time-dependent parameter of the swirled blood flow corresponding to the normal indicator for the diastolic flow.

The pump valves may have the design of the cardiac valve prostheses described above.

The pump channel may have the design of the cannula described above.

The swirling device comprises an end piece having a streamlined surface provided with guides in the form of ribs, grooves or blades shaped in accordance with formulas (1.1 to 1.3), the swirling angle of the flow being varied optionally by the operator or by a device capable of modeling different flow conditions.

The swirling device surfaces washed over by blood may be provided with a relief consisting of areas of originally smooth surface alternating with curved areas in the form of depressions, each formed by quadric convex and concave surfaces joined along common tangents. Moreover, a depression is joined to the originally smooth surface by convex surfaces producing slopes, for which the originally smooth surface in the joint areas is a tangent.

The Method is Performed by:

measuring the blood flow velocity field in the patient's heart chambers and great vessels; modeling the individual blood flow in the circulation system being diagnosed by using a hydrodynamic model and software tools based on the exact solutions on non-stationary hydrodynamic equations for spout-like swirled fluids of incompressible viscous fluids, the components $V_z$, $V_r$ and $V_\phi$ thereof being represented for the dominant swirled stream by equations (3.1, 3.2, and 3.3), and by equations (2.1, 2.2, and 2.3) for the full stream in the aorta; or mapping the blood flow velocity field in the patient's heart chambers and vessels by any methods, including ultrasonic and magnetic resonance techniques; processing the results using software tools based on the exact solutions of non-stationary hydrodynamic equations; calculating the characteristic parameters of an individual swirled flow using the mapping results and the assessment results of the conditions of the blood circulation system obtained by routine methods; and identifying localization of pathological changes in the blood flow and the degree in which the flow structure deviates from the individual physiological norm;

using the analysis performed as a basis to assess the extent of required surgical correction of the geometry of the heart chambers in the blood channel; choosing the surgery tactic in order to achieve a longitudinally radial and radially azimuthal vessel cross-sections at every point along the blood flow, with a maximum approximation to the following formulas:

in the longitudinally radial plane:

$$[Z_0(t) + z_i]r_i^2 = Q_0(t) \tag{4.1}$$

$$\varphi_i = \Phi_0(t) + \frac{\Gamma_0(t)}{4\pi R_0(t)^2 C_0(t)}\left[\frac{z_i}{Z_0(t)} - 1\right];$$

in the radially azimuthal plane:

$$[Z_0(t) + z_i]r_i^2 = Q_0(t) \tag{4.2}$$

$$\varphi_i = \Phi_0(t) + \frac{\Gamma_0(t)}{4\pi R_0(t)^2 C_0(t)}\left[\frac{R_0(t)^2}{r_i^2} - 1\right];$$

wherein: $z_i$, $r_i$, $\phi_i$, $Z_0(t)=z-z_i$, $R_0(t)=r-r_i$, $\Gamma_0(t)$, $C_0(t)$, $\Phi_0(t)=\phi_i(t)-\{[\Gamma_0(t)4\pi R_0(t)^2 C_0(t)]$ and $[(R_0(t)^2/r_i^2)-1]\}$ are as defined above; and $Q_0(t)$ is a function proportional to the volume of the swirled blood stream that varies cyclically depending on the cardiac contraction phase, the instantaneous values of $Q_0(t)$ being constant over the full length of the blood channel at any time moment and calculated from the velocity field mapping data of the swirled blood flow;

using the combined results of diagnostics, calculated data, and blood flow modeling results to treat surgically the pathologically altered segment of the blood circulation system by selecting an optimal tactic for geometrical reconstruction and/or designing of a prosthesis of the damaged channel segment to restore the shape adequate to the physiologically normal swirled flow by correcting the geometrical parameters and/or covering the streamlined surface with a guide relief selected on the basis of a hydrodynamic model, and directing the flow into the channel so that the flow velocity and pressure fields are combined with similar fields existing in the patient's blood circulation system;

using the combined results of diagnostics, calculated data, and blood flow modeling results to apply cardio-surgical treatment to the damaged segments of the patient's cardiovascular system requiring connection to artificial blood circulation devices and/or use of other para-corporeal devices having flow channels of geometrical shapes and reliefs optimized with the purpose of combining the velocity and pressure fields in the patient's blood circulation system with the velocity and pressure field in the devices connected thereto, the shape of the connected circuit being modeled on the basis of a hydrodynamic model using the values of the quantities $Q_0(t)$, $\Gamma_0(t)$, $C_0(t)$, $Z_0(t)$, $R_0(t)$, and $\Phi_0(t)$ measured by diagnosing the blood flow in the patient's organism, and the para-corporeal circulation device is equipped with a suitable control system monitoring the characteristics of the swirled blood flow and geometric configuration of the elastic vessels of the circuit for approximating the blood flow parameters in the device to the flow parameters in the patient's blood circulation system on the basis of formulas (4.1) и(4.2);

using the combined results of diagnostics, calculated data, and blood flow modeling results to apply cardio-surgical treatment requiring a pump to be connected for assist circulation or a fully implantable artificial heart, in which the geometrical shapes and reliefs of flow channels are optimized to combine the velocity and pressure field in the devices connected as above with the velocity and pressure field of the patient's blood circulation system, the shape of the resultant flow channel being modeled on the basis of a hydrodynamic model using the values of the quantities $Q_0(t)$, $\Gamma_0(t)$, $C_0(t)$, $Z_0(t)$, $R_0(t)$, and $\Phi_0(t)$ measured by diagnosing the blood flow in the patient's organism, and the devices are equipped with a suitable control system monitoring the characteristics of the swirled blood flow and the geometric configuration of the vessels of the circuit to approximate the blood flow parameters in the device to the flow parameters in the patient's blood circulation system on the basis of formulas (4.1) и(4.2); and monitoring the efficiency of the surgical treatment applied by measuring the extent of conformity of the swirled blood flow structure to the patient's individual norms by analyzing the post-surgical mapping data of the velocity field in the blood flow and by routine diagnostic techniques and methods.

Figure 1:
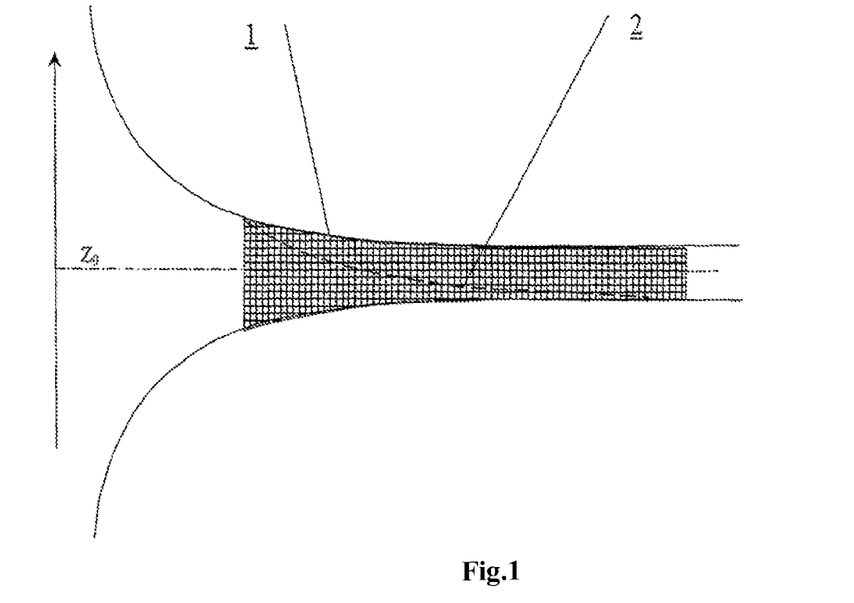
FIG. 1 is a view of a vessel prosthesis.
Figure 2:
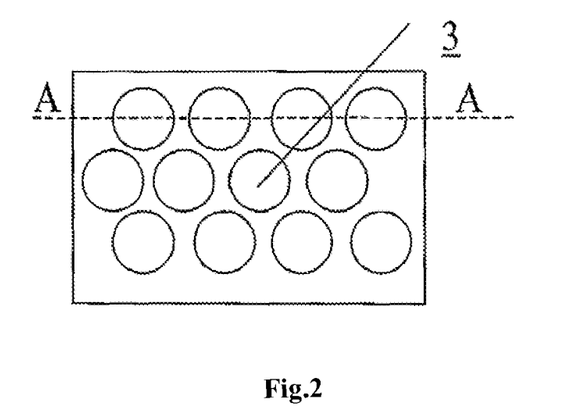
FIG. 2 shows location of depressions on the internal surface of the vessel.
Figure 3:
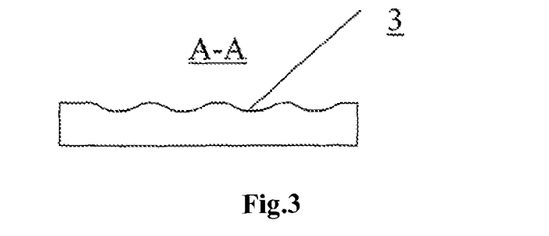
FIG. 3 is a sectional view along A-A in FIG. 2.

Implementation of the Flow Formation Method is Illustrated in the Following Description of Embodiments of the Devices:

A vessel prosthesis comprises a tube 1 provided on the internal surface thereof with a relief 2 to swirl the blood flow (FIG. 1). The internal surface of the tube may be provided with a relief consisting of areas of originally smooth surface alternating with curved areas in the form of depressions 3. The prosthesis may be either rigid or have elastic walls.

Figure 4:
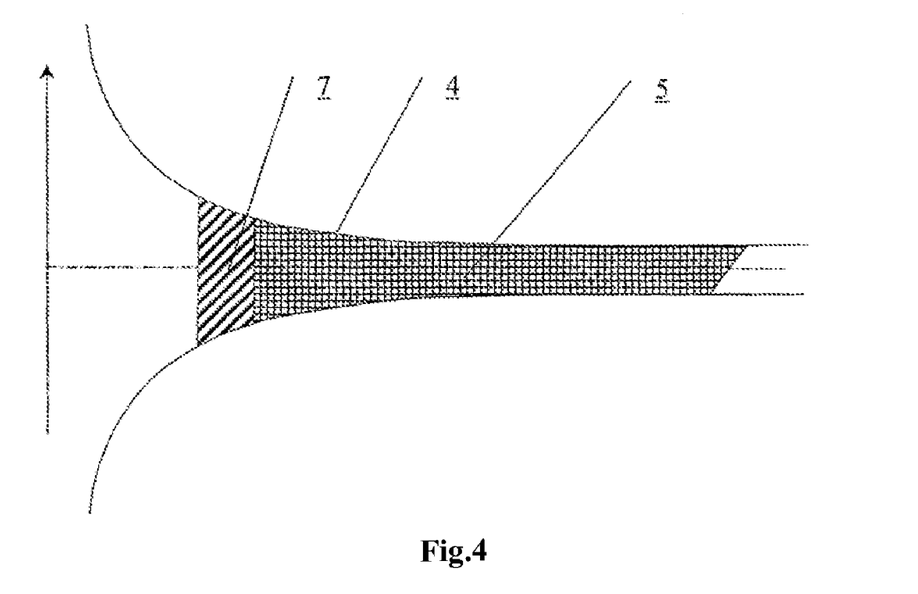
FIG. 4 is a view of a cannula.
Figure 5:
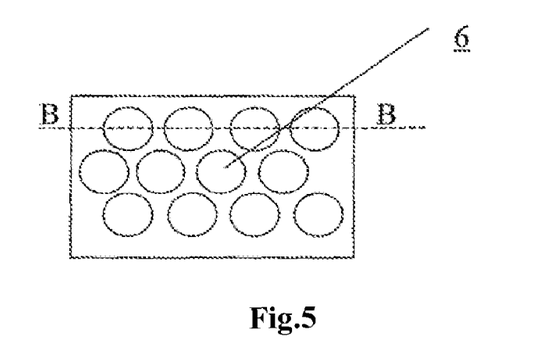
FIG. 5 shows location of depressions on the internal surface.
Figure 6:
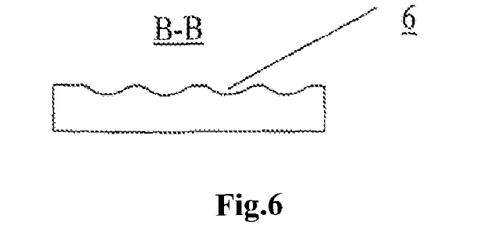
FIG. 6 is a sectional view along B-B in FIG. 5.
Figure 7:
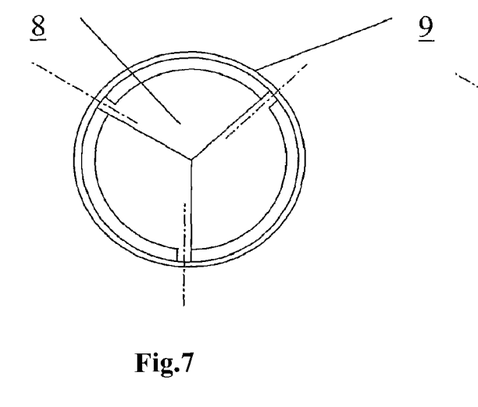
FIG. 7 is a view of a closed heart valve.
Figure 8:
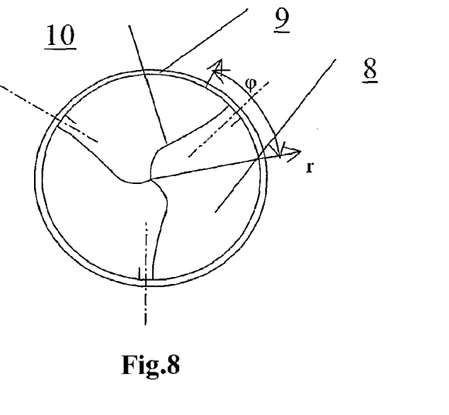
FIG. 8 is a view of an open heart valve.
Figure 9:
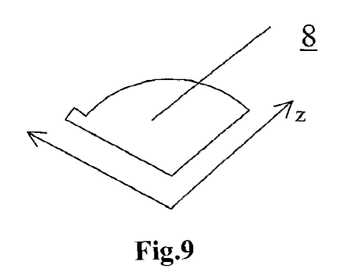
FIG. 9 is a view of the heart valve cusp.
Figure 10:
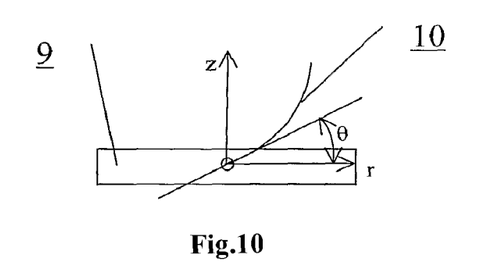
FIG. 10 is a sectional view of the valve with an open cusp.
Figure 11:
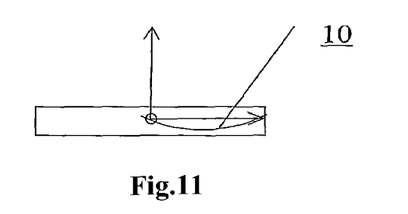
FIG. 11 is a sectional view of the valve with a closed cusp.
Figure 12:
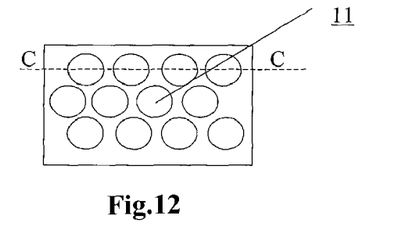
FIG. 12 shows location of depressions on the internal surface.
Figure 13:
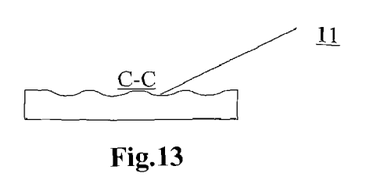
FIG. 13 is a sectional view along C-C in FIG. 12.

A cannula has a flow channel 4 provided on the internal surface thereof with a longitudinal relief 5 to swirl the blood flow (FIG. 4). The internal surface may be provided with a relief consisting of areas of originally smooth surface alternating with curved areas in the form of depressions 6. A part of the cannula channel may be provided with guides in the form of ribs, grooves or blades having an adjustable swirling angle. The cannula may be made of an elastic material. The cannula may be used in combination with a swirling device 7.

A heart valve prosthesis comprises one or more shutoff elements 8 placed in a symmetrical central position within a body 9 of a round and/or oval cross-section (FIGS. 7 to 11). The streamlined edge of the valve shutoff element is to correspond in the open position to a relief 10 duplicating the flow line orientation of the swirled blood current. The streamlined surfaces may be provided with a relief consisting of areas of originally smooth surface alternating with curved areas in the form of depressions 11.

Figure 14:
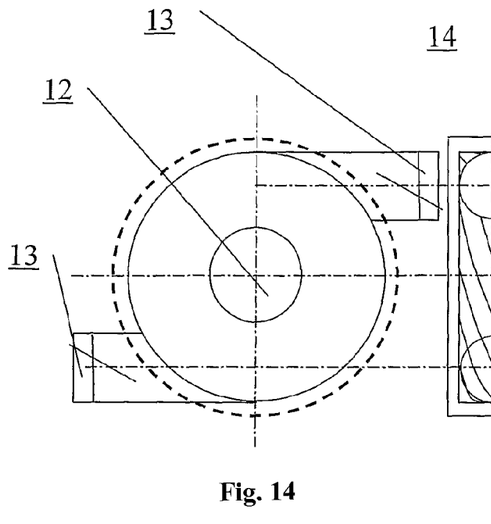
FIG. 14 is a cross-sectional view of the pump.
Figure 15:
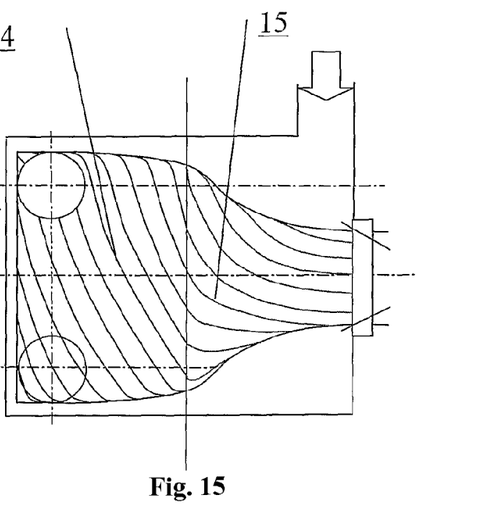
FIG. 15 is a longitudinal sectional view of the pump.
Figure 16:
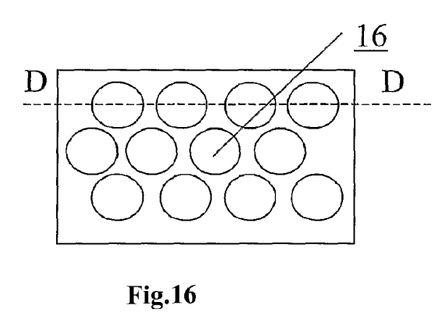
FIG. 16 shows location of depressions on the internal surface.
Figure 17:
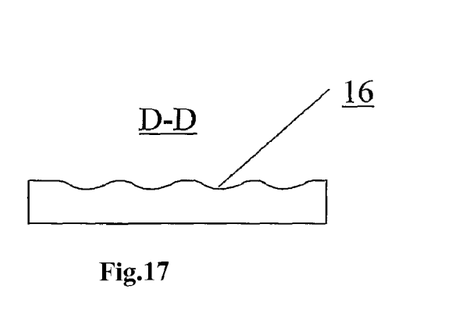
FIG. 17 is a sectional view along D-D in FIG. 16.

A blood pump comprises a flow channel 12 and valves 13 at the channel inlet and outlet (FIG. 14 and FIG. 15). The streamlined surface of the pump inlet part is provided with a pattern 14 to swirl the blood flow filling the pump. The streamlined pump outlet part is provided with a pattern 15 to swirl the blood flow expelled from the pump. The streamlined surfaces may be provided with a relief consisting of areas of originally smooth surface alternating with curved areas in the form of depressions 16. The inlet and/or outlet part(s) of the flow channel may be provided with ribs, grooves or blades having an adjustable swirling angle.

Figure 18:
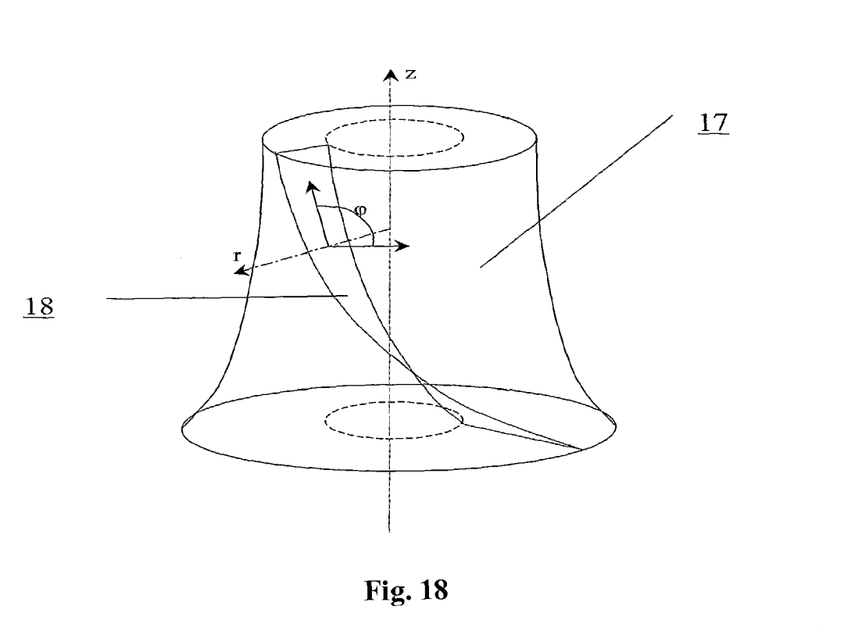
FIG. 18 is a view of a swirling device.
Figure 19:
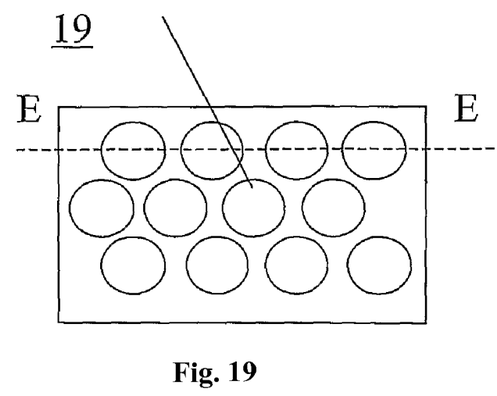
FIG. 19 shows location of depressions on the internal surface of the swirling device.
Figure 20:
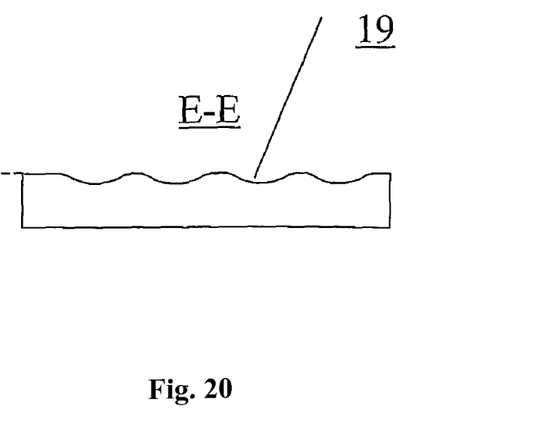
FIG. 20 is a sectional view along E-E in FIG. 19.

The swirling device is designed as an end piece 17 having a streamlined surface that is provided with guides 18 in the form of ribs, grooves or blades having an adjustable inclination angle to swirl the flow. The streamlined surfaces may be provided with a relief 19 consisting of areas of originally smooth surface alternating with curved areas in the form of depressions.

The pumps and flow lines of an assist artificial heart ventricle, artificial blood circulation devices, fully implantable artificial heart, and/or other para-corporeal devices are calculated, designed, and manufactured in accordance with formulas (1.1 to 1.3; 2.1 to 2.3; 3.1 to 3.3; and 4.1-4.2), and the flow channels in contact with the blood flow in these devices may be removable and are, in need, manufactured individually for every patient, the elasticity, geometric forms, size, and surface relief of these channels being calculated, designed, and manufactured in accordance with the values of the quantities $Q_0(t)$, $\Gamma_0(t)$, $C_0(t)$, $Z_0(t)$, $R_0(t)$, and $\Phi_0$ measured at the time when the blood circulation condition is diagnosed. As a result, a swirled spout-like blood flow corresponding to an individual physiological norm is formed in these devices. In this case, a flow formed according to the above formulas meets the conditions required for combining the velocity and pressure field in a connected device with the velocity and pressure field in the patient's blood flow that is formed by the patient's heart as the assist and/or artificial blood circulation is disconnected. Moreover, the artificial and assist blood circulation devices and the implantable artificial heart designed in accordance with formulas (1.1 to 1.3; 2.1 to 2.3; 3.1 to 3.3; and 4.1-4.2) form a swirled blood flow consistent with the individual physiological norm over the full implantation period.

The aforesaid devices operate as follows:

Implantable or para-corporeal devices (vessel prostheses, valve prostheses, artificial heart, assist blood circulation devices, cannulas, and artificial blood circulation devices) are inserted into the blood vessel by direct connection; and devices manufactured in accordance with formulas (1.1 to 1.3; 2.1 to 2.3; 3.1 to 3.3; and 4.1-4.2) for use in testing and research stands for flow swirling are inserted directly into a circulation circuit simulating blood circulation conditions.

The relief applied to the streamlined surface forms a swirled blood or model fluid current in accordance with the Kiknadze-Krasnov solutions by interacting with the viscous flow.

This structural flow organization helps produce a physiologically adequate blood or model fluid current free from stagnation and flow separation zones.

INDUSTRIAL APPLICABILITY

The invention can be used for:

developing software tools to be used for measuring a blood flow with research and/or medical purposes by any methods, including ultrasonic and magnetic resonance methods;

selecting physiological blood circulation norms in respect of the swirled blood flow structure for a representative standard sample of volunteers;

measuring and identifying individual structural organization of the blood flow in a patient's heart and great vessels;

planning and carrying out reconstructive heart surgeries undertaken to restore the normal geometry of a patient's blood channel maintaining the swirled blood flow structure;

developing mathematical support and software tools for individual selection of the design of implantable organ-substituting devices maintaining a normal swirled structure of a patient's blood flow;

designing organ-substituting devices for cardiovascular surgery (heart valve and vessel prostheses) that restore adequate geometry of a patient's blood channel, and have a heightened safety owing to the formation of a swirled blood flow structure;

designing implantable and para-corporeal pumps for assist blood circulation and a fully implantable artificial heart, and also devices for connecting them, so that a swirled blood flow is formed inside the pump and the swirled blood flow structure is maintained in the blood circulation system in order to improve the efficiency and safety of these devices;

designing para-corporeal pumps and circuits (artificial blood circulation devices, para-corporeal systems supporting vital functions such as artificial kidney, artificial liver, and so on), their conduits and accessories (cannulas, heat exchangers, filters, and so on), forming and maintaining a swirled blood flow structure in order to improve the efficiency and safety of these devices;

designing research stands for physical and mathematical modeling of various blood circulation conditions for research purposes in respect of the swirled structure of a physiological blood flow;

designing testing stands for assessing the functional properties of implantable organ-substituting devices for cardiovascular surgery in the presence of a swirled flow of model fluid or blood of desired characteristics; and designing a special-purpose streamlined surface in the above-said devices in order to create conditions for current in the boundary layer to prevent activation of the blood-clotting system and complement system, sedimentation, and accumulation of blood components, injury to cellular blood elements, and other phenomena capable of causing hemolysis, pathological immune response, thrombosis, and hyperplasia.

What is claimed is:

1. A vessel prosthesis comprising a tube having an internal surface that is provided with a pattern for swirling the blood flow in accordance with formulas:

$$Q(t) = \lfloor z + Z_0(t) \rfloor r^2$$

$$\varphi = \varphi_0 + k(t)z$$

$$k(t) = \frac{\Gamma_0(t)}{4\pi Q(t) C_0(t)}$$

wherein: $\varphi_0$ is the initial swirling angle in relation to the flow axis normal; $\varphi$, z and r are current values of the angular, longitudinal, and radial coordinates along the flow line; $Q(t), Z_0(t), k(t), \Gamma_0(t)$, and $C_0(t)$ are parameters of a non-stationary swirled blood flow and geometry of the blood channel that depend on time because of non-stationary current and correspond to the individual normal indicators of the swirled blood flow measured by routine examination of a representative sample of patients showing no changes in the blood circulation system for a specific localization of the segment to be replaced with a prosthesis.

2. The prosthesis as claimed in claim 1, wherein the internal surface thereof is provided with a relief consisting of areas of originally smooth surface alternating with curved areas in the form of depressions, each formed by quadric convex and concave surfaces joined along common tangents, a depression being joined to the originally smooth surface by convex surfaces producing slopes for which the originally smooth surface in the joint areas is a tangent.

3. The prosthesis as claimed in claim 2, wherein the tube is made of an elastic bio- and hemo-compatible material, for example, a woven synthetic fabric, that makes the shape of the flow section of the blood flow channel consistent with the normal blood flow parameters Q(t) and $Z_0(t)$ along the vessel channel over the full cardiac cycle.

4. A cannula for para-corporeal perfusion devices comprising an angled pointed tip, a swirling device, and a flow channel having an internal surface that is provided with a longitudinal pattern for swirling the blood flow in accordance with formulas:

$$Q(t) = |z + Z_0(t)|r^2$$

$$\varphi = \varphi_0 + k(t)z$$

$$k(t) = \frac{\Gamma_0(t)}{4\pi Q(t) C_0(t)}$$

wherein: $\varphi_0$ is the initial swirling angle in relation to the flow axis normal; $\varphi$, z and r are current values of the angular, longitudinal, and radial coordinates along the flow line; $Q(t), Z_o(t), k(t), \Gamma_o(t)$, and $C_o(t)$ are parameters of a non-stationary blood flow and geometry of the blood channel that depend on time because of non-stationary current and correspond to the individual normal indicators of the swirled blood flow measured by routine examination of a representative sample of patients showing no changes in the blood circulation system for a specific localization of the point where the cannula is inserted into the vessel channel.

5. The cannula as claimed in claim 4, wherein the internal surface thereof is provided with a relief consisting of areas of originally smooth surface alternating with curved areas in the form of depressions, each formed by quadric convex and concave surfaces joined along common tangents, a depression being joined to the originally smooth surface by convex surfaces producing slopes for which the originally smooth surface in the joint areas is a tangent.

6. The cannula as claimed in claim 4, wherein at least a part of the channel is provided with guides in the form of ribs, or grooves, or blades at a swirling angle:

$$\varphi = \varphi_0 + k(t)z,$$

wherein: $\varphi_0$ is the initial swirling angle in relation to the flow axis normal; $\varphi$ and z are current values of the angular and longitudinal coordinates along the flow line; and k(t) is a parameter of a non-stationary swirled blood flow that corresponds to the individual normal indicators for a specific localization of the point where the cannula is inserted into the vessel channel.

7. The cannula as claimed in claim 4 made of an elastic material, wherein its flexibility results in consistency of the parameters Q(t) and $Z_0$(t) with the individual normal indicators along the flow channel at each moment of the cardiac cycle.

8. A heart valve prosthesis, comprising one or more shutoff elements arranged symmetrically at the center of a body of round and/or oval cross-section, the streamlined surfaces of the valve being provided with a pattern in accordance with formulas:

$$Q(t) = \lfloor z + Z_0(t) \rfloor r^2$$
$$\varphi = \varphi_0 + k(t)z$$
$$k(t) = \frac{\Gamma_0(t)}{4\pi Q(t) C_0(t)}$$

wherein: $\phi_0$ is the initial swirling angle in relation to the flow axis normal; $\phi$, z and r are current values of the angular, longitudinal, and radial coordinates along the flow line; Q(t), $Z_0$(t), k(t), $\Gamma_0$(t), and $C_0$(t) are parameters of a non-stationary blood flow and geometry of the blood channel that depend on time because of non-stationary current and correspond to the individual normal indicators of the swirled blood flow measured by routine examination of a representative sample of patients showing no changes in the blood circulation system for a given position of the valve.

9. The prosthesis as claimed in claim 8, wherein the streamlined surface of the shutoff elements and body is provided with a relief consisting of areas of originally smooth surface alternating with curved areas in the form of depressions, each formed by quadric convex and concave surfaces joined along common tangents, a depression being joined to the originally smooth surface by convex surfaces producing slopes for which the originally smooth surface in the joint areas is a tangent.

10. A blood pump comprising a flow compression unit, a flow channel, and valves at the inlet and outlet of the channel, the surface washed over by blood being provided with a pattern in accordance with formulas:

$$Q(t) = |z + Z_0(t)| r^2$$
$$\varphi = \varphi_0 + k(t)z$$
$$k(t) = \frac{\Gamma_0(t)}{4\pi Q(t) C_0(t)}$$

wherein: $\phi_0$ is the initial swirling angle in relation to the flow axis normal; $\phi$, z and r are current values of the angular, longitudinal, and radial coordinates along the flow line; Q(t), $Z_o$(t), k(t), $\Gamma_o$(t), and $C_o$(t) are parameters of a non-stationary blood flow and geometry of the blood channel that depend on time because of non-stationary current and correspond to the individual normal indicators of the swirled blood flow measured by routine examination of a representative sample of patients showing no changes in the blood circulation system.

11. The pump as claimed in claim 10, wherein the surfaces washed over by blood are provided with a relief consisting of areas of originally smooth surface alternating with curved areas in the form of depressions, each formed by quadric convex and concave surfaces joined along common tangents, a depression being joined to the originally smooth surface by convex surfaces producing slopes for which the originally smooth surface in the joint areas is a tangent.

12. The pump as claimed in claim 10, further comprising on the outlet part of the streamlined surface of the flow channel guides in the form of ribs, or grooves, or blades at a swirling angle:

$$\phi = \phi_0 + k(t)z,$$

wherein: $\phi_0$ is the initial swirling angle in relation to the flow axis normal; $\phi$ and z are current values of the angular and longitudinal coordinates along the flow line; and $k_s$(t) is a parameter of a swirled blood flow variable over time that corresponds to the normal indicator for the systolic flow.

13. The pump as claimed in claim 10, wherein the inlet part of the streamlined surface is provided with guides in the form of ribs, or grooves, or blades at a swirling angle:

$$\phi = \phi_0 + k_d(t)z,$$

wherein: $\phi_0$ is the initial swirling angle in relation to the flow axis normal; $\phi$ and z are current values of the angular and longitudinal coordinates along the flow line; and $k_d$(t) is a parameter of a swirled blood flow variable over time that corresponds to the normal indicator for the diastolic flow.

14. A pump as claimed in claim 10, wherein the valves at the inlet or outlet thereof are heart valve prostheses; the heart valve prosthesis comprising one or more shutoff elements arranged symmetrically at the center of a body of round and/or oval cross-section, the streamlined surfaces of the valve being provided with a pattern in accordance with formulas:

$$Q(t) = [z + Z_0(t)] r^2$$
$$\varphi = \varphi_0 + k(t)z$$
$$k(t) = \frac{\Gamma_0(t)}{4\pi Q(t) C_0(t)}$$

wherein: $\phi_0$ is the initial swirling angle in relation to the flow axis normal; z and r are current values of the angular, longitudinal, and radial coordinates along the flow line; Q(t), $Z_0$(t), k(t), $\Gamma_0$(t), and $C_0$(t) are parameters of a non-stationary blood flow and geometry of the blood channel that depend on time because of non-stationary current and correspond to the individual normal indicators of the swirled blood flow measured by routine examination of a representative sample of patients showing no changes in the blood circulation system for a given position of the valve.

15. The pump as claimed in claim 10, wherein the cannulas and channels each comprise a flow channel having an internal surface that is provided with a longitudinal pattern for swirling the blood flow in accordance with formulas:

$$Q(t) = [z + Z_0(t)]r^2$$

$$\varphi = \varphi_0 + k(t)z$$

$$k(t) = \frac{\Gamma_0(t)}{4\pi Q(t)C_0(t)}$$

wherein: $\phi_0$ is the initial swirling angle in relation to the flow axis normal; $\phi$, z and r are current values of the angular, longitudinal, and radial coordinates along the flow line, $Q(t)$, $Z_0(t)$, $k(t)$, $\Gamma_0(t)$, and $C_0(t)$ are parameters of a non-stationary blood flow that correspond to the individual normal indicators for a specific localization of the point where the cannula is inserted into the vessel channel.

\* \* \* \* \*

UNITED STATES PATENT AND TRADEMARK OFFICE
CERTIFICATE OF CORRECTION

PATENT NO.         : 8,123,670 B2
APPLICATION NO.    : 12/672657
DATED              : February 28, 2012
INVENTOR(S)        : Bokeriya et al.

Page 1 of 1

It is certified that error appears in the above-identified patent and that said Letters Patent is hereby corrected as shown below:

On the Coversheet Item (54) and in Column 1, lines 1-5, the Title of the Invention reads:

"METHOD FOR FORMING A BLOOD FLOW IN SURGICALLY RECONSTITUTED SEGMENTS OF THE BLOOD CIRCULATORY SYSTEM AND DEVICES FOR CARRYING OUT SAID METHOD"

should read

-- METHOD FOR FORMING A BLOOD FLOW IN SURGICALLY RECONSTRUCTED SEGMENTS OF THE BLOOD CIRCULATORY SYSTEM AND DEVICES FOR CARRYING OUT SAID METHOD --

Column 7, line 61, reads "model fluid having a desire velocity and pressure field corre-"
    should read -- model fluid having a desired velocity and pressure field corre- --

Column 10, line 40, reads "larly by formulas (2.1 to 2.3). The dominant steam has a"
    should read -- larly by formulas (2.1 to 2.3). The dominant stream has a --

Column 12, line 10, reads "with formulas (1.1 to 1.3 an 3.1 to 3.3)."
    should read -- with formulas (1.1 to 1.3 and 3.1 to 3.3). --

Column 15, line 24, reads "treatment requiring a pump to be connected for assist"
    should read -- treatment requiring a pump to be connected to assist --

Column 17, line 26, reads "designing implantable and para-corporeal pumps for assist"
    should read -- designing implantable and para-corporeal pumps to assist --

Signed and Sealed this
Eighth Day of May, 2012

David J. Kappos
*Director of the United States Patent and Trademark Office*